(12) United States Patent
Ellis

(10) Patent No.: US 11,911,526 B1
(45) Date of Patent: Feb. 27, 2024

(54) DRINKING STRAW SANITIZING APPLIANCE

(71) Applicant: Daniel K. Ellis, Tempe, AZ (US)

(72) Inventor: Daniel K. Ellis, Tempe, AZ (US)

( * ) Notice: Subject to any disclaimer, the term of this patent is extended or adjusted under 35 U.S.C. 154(b) by 525 days.

(21) Appl. No.: 16/748,355

(22) Filed: Jan. 21, 2020

Related U.S. Application Data

(60) Provisional application No. 62/795,074, filed on Jan. 22, 2019.

(51) Int. Cl.
*A47G 21/18* (2006.01)
*A61L 2/07* (2006.01)
*B08B 3/10* (2006.01)
*A61L 2/24* (2006.01)

(52) U.S. Cl.
CPC .................. *A61L 2/07* (2013.01); *A61L 2/24* (2013.01); *B08B 3/10* (2013.01); *A47G 21/18* (2013.01); *A61L 2202/11* (2013.01); *A61L 2202/121* (2013.01); *A61L 2202/122* (2013.01); *A61L 2202/14* (2013.01); *A61L 2202/17* (2013.01); *B08B 2203/007* (2013.01)

(58) Field of Classification Search
CPC .......... A61L 2/07; A61L 2/24; A61L 2202/11; A61L 2202/121; A61L 2202/122; A61L 2202/14; A61L 2202/17; B08B 3/10; B08B 2203/007; A47G 21/18
See application file for complete search history.

(56) References Cited

U.S. PATENT DOCUMENTS

| | | |
|---|---|---|
| 3,982,296 A | 9/1976 | Russo |
| 4,403,364 A | 9/1983 | Schroeder |
| D360,301 S | 7/1995 | Hogle |
| 5,652,991 A | 8/1997 | Kashani |
| 5,715,565 A | 2/1998 | Kern |
| 6,039,490 A | 3/2000 | Banks et al. |
| D532,978 S | 12/2006 | Robinson |
| D658,893 S | 5/2012 | Reyes |
| 8,403,172 B1 | 3/2013 | Kelley et al. |
| 8,672,128 B2 | 3/2014 | Davis |
| 9,265,334 B1 | 2/2016 | Fung-A-Wing |
| 10,058,169 B2 | 8/2018 | Gorelick |
| 10,932,647 B1 * | 3/2021 | Audibert ............... A47L 15/505 |
| 2013/0081653 A1 * | 4/2013 | Kountotsis ............... B08B 7/00 134/8 |
| 2020/0086363 A1 * | 3/2020 | Bowman ............. A47L 15/0089 |
| 2021/0001385 A1 * | 1/2021 | Bowman ............. A47L 15/0089 |

FOREIGN PATENT DOCUMENTS

| | | | |
|---|---|---|---|
| CN | 105877666 A | * | 8/2016 |
| JP | 5574885 B2 | * | 8/2014 |

\* cited by examiner

*Primary Examiner* — Alexander Markoff
(74) *Attorney, Agent, or Firm* — Cramer Patent & Design PLLC; Aaron R. Cramer

(57) ABSTRACT

A drinking straw sanitizing appliance includes an exterior housing defining an interior having an adjustable heating element configured to covert a unit of water into steam. The interior is configured to also removable secure drinking straws therein thereby subjecting the same to sanitizing steam when the device is activated. The exterior of the device has a plurality of controls and a lid of the device has a locking mechanism.

17 Claims, 4 Drawing Sheets

DRINKING STRAW SANITIZING APPLIANCE

RELATED APPLICATIONS

The present invention is a Continuation of and claims the benefit of U.S. Application No. 62/795,074, filed Jan. 22, 2019, the entire disclosures of which are incorporated herein by reference.

FIELD OF THE INVENTION

The present invention relates to a sanitizing appliance and more specifically to a drinking straw sanitizing appliance.

BACKGROUND OF THE INVENTION

Just about everyone loves the tastes of an ice-cold beverage such as soda, iced tea, or even water. Most people drink such beverages with the use of a straw since a drink lid, sanitary issues, or other reasons require straw usage. This means that the cup contents, the surface of the beverage, and the entire interior of the cup is protected from contact with foreign material. However, many people are now becoming more aware of the damage being inflicted by straws upon the environment due to tons of straws in landfills. Turtles and other aquatic life also suffer should the straws end up in bodies of water.

The market has responded to this issue with straws that can be reused, however, many remain squeamish due to the difficulty in ensuring the interior of the reusable straw is sanitized before being reused by another customer. Accordingly, there exists a need for a means by which reusable drinking straws can be sanitized in an effort to address the concerns as outlined above. The development of the drinking straw sanitizing appliance fulfills this need.

BRIEF SUMMARY OF THE INVENTION

The principles of the present invention provide for a drinking straw sanitizing appliance which comprises a receptacle having a heating element, a basket removably placed within the receptacle, a lid hingedly attached at a first edge to an upper edge of the rear wall of the receptacle and secured attached at a second edge to an upper edge of the front wall of the receptacle with at least one latch, a vent having a vent door with a vent handle that opens or closes over the vent, a timer control circuit in electrical communication with a power switch, an adjustable thermostat, and the heating element, a first indicator light and a second indicator light provided in electrical communication with the power switch, a pan holding the water or cleaning solution therein adjacent to the heating element and a fill line imprinted about a circumferential inner surface of the pan to indicate a maximum amount of the water or cleaning solution placed therein without incidental contact of the water or cleaning solution onto the straws.

The receptacle includes a bottom wall, a pair of side walls, a front wall, a rear wall, and an open top providing access to an interior. The basket secures a plurality of drinking straws there within for cleaning, the basket includes a basket top, a basket bottom, a pair of basket short sides, and a pair of basket long sides, to create a six-sided structure. The lid when secured with the at least one latch to effectively provides a seal to the environment from the interior of the drinking straw sanitizing appliance. The lid also covers an interior of the drinking straw sanitizing appliance.

The heating element is located on a floor of the receptacle to heat water or a cleaning solution in a steaming temperature or an elevated sanitizing temperature to render the drinking straws sanitary for reuse. The heating element is in electrical communication with a power supply via the power switch and the adjustable thermostat. A shelf holds the basket that is located superjacent to the heater element and circumscribing an inner surface of the receptacle. The receptacle may be a rectangular prism. The basket top may include a plurality of apertures formed thereon sized to permit passage of an individual straw therethrough. The basket may be made of a metallic or plastic mesh.

The timer control circuit may be pre-determined to enable a supply of power from a power source to the heating element to affect a cleaning period. The first indicator light may preferably indicate that the drinking straw sanitizing appliance is working and may be a green LED. The second indicator light may indicate that the drinking straw sanitizing appliance is off and may be a red LED. The power switch, the adjustable thermostat, the first indicator light, and the second indicator light may be located on a front facing of the receptacle. The heating element may be embedded to the floor of the receptacle. The heating element may be attached to the floor of the receptacle. The power switch provides a selective power to the heating element from the power supply. The adjustable thermostat may provide a temperature regulating means. The temperature regulating means may be used in place of the adjustable thermostat. The temperature regulating means may be a temperature regulator which may be selected from the group of a rheostat, a potentiometer, or a solid-state controller.

The power source may be an integral battery. The power source may be a power cord or an electrical outlet. The basket bottom may have a mesh or a grid-like construction having a plurality of apertures that do not permit the straws from falling through and functions to effectively block the heating element from physical contact with the straws in the basket and maintains a vertical upright orientation for the straws to maximize a sanitizing event.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
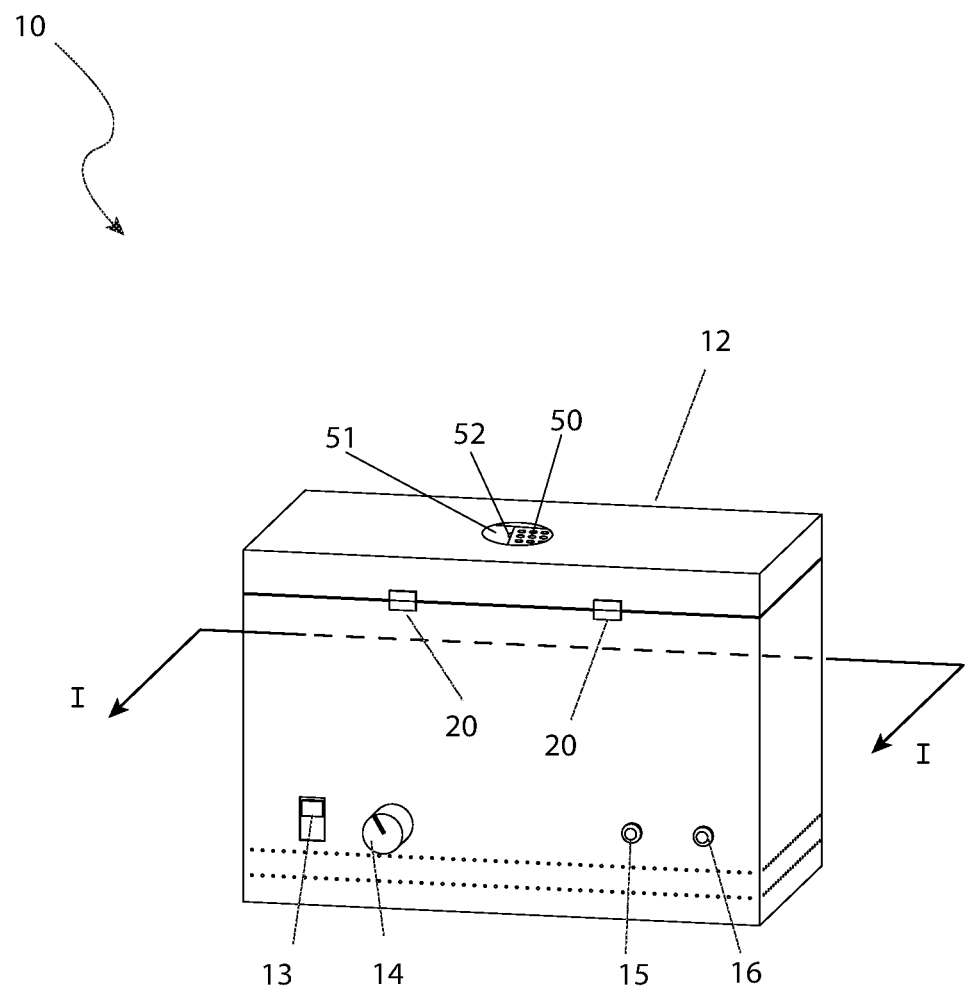
FIG. 1 is a top perspective view of the drinking straw sanitizing appliance 10, according to the preferred embodiment of the present invention.

DESCRIPTIVE KEY 10 drinking straw sanitizing appliance
11 receptacle
12 lid
13 power switch 14 adjustable thermostat
15 first indicator light
16 second indicator light
20 latch
21 interior
23 door
25 heating element
30 tray
31 fill line
40 basket
41 basket top
42 basket bottom
43 basket short side
44 basket long side
45 aperture
48 handle
50 vent
51 vent door
52 vent handle
60 power source
65 thermal overload protector
70 timer control circuit
100 straw 1. Description of the Invention The best mode for carrying out the invention is presented in terms of its preferred embodiment, herein depicted within FIG. 1. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

Referring now to FIG. 1, a top perspective view of the drinking straw sanitizing appliance (herein described as the "appliance") 10. The appliance 10 is particularly suited for on-demand sanitizing of at least one (2) drinking straw 100, or more preferably, a plurality of drinking straws 100, in an on-the-counter style of appliance 10 that is easy to use, convenient, automatic, and unobtrusive. The appliance includes a receptacle 11 with a heating element 25 and a lid 12 for covering the interior 21 of the appliance 10, and a basket 40 that is capable of removable placement within the receptacle 11. The appliance 10 is capable of securing a plurality of drinking straws 100 therewithin for subsequent cleaning. The heating element 25 is located in the floor of the receptacle 11 and can heat water or a cleaning solution in a steaming or an elevated sanitizing temperature to render the drinking straws 100 sanitary for subsequent re-use.

Figure 2:
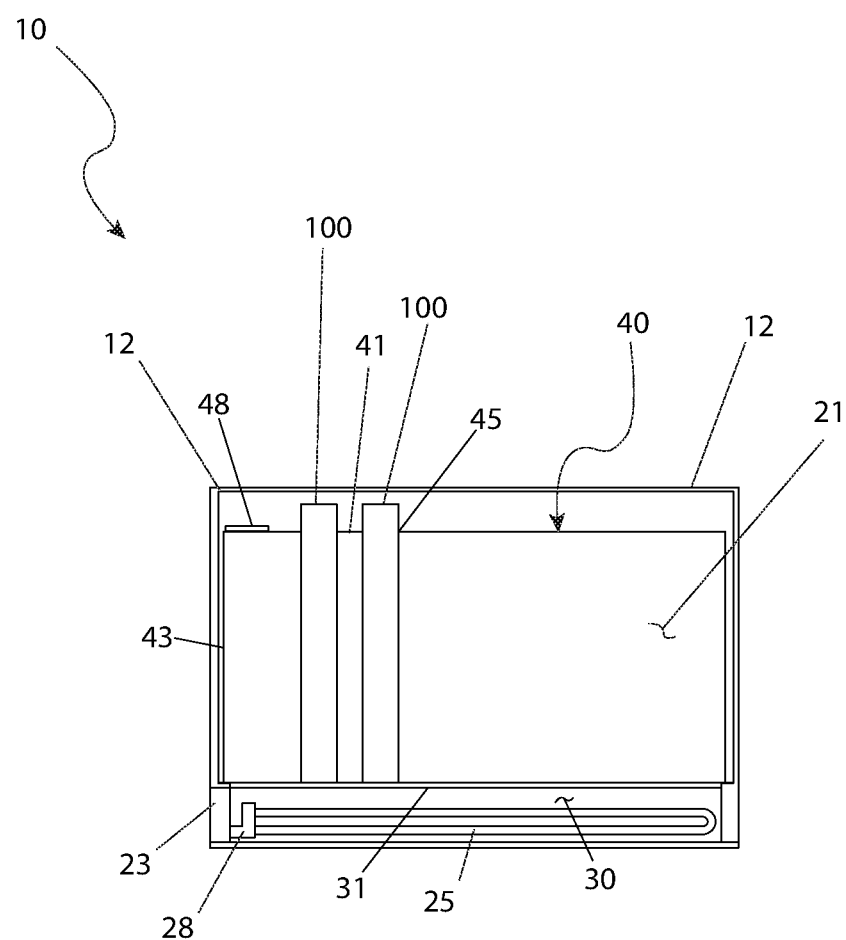
FIG. 2 is a cut-away view along the line I-I (see FIG. 1) of the interior 21 of the drinking straw sanitizing appliance 10, according to the preferred embodiment of the present invention.

Referring further to FIG. 1, as well as referring FIG. 2, which is a cut-away of the appliance 10; in a preferred embodiment, the receptacle 11 is a rectangular prism, having a bottom wall, a pair of side walls, a front wall, a rear wall, and an open top providing access to an interior 21 thereof.

A lid 12 is hingedly attached at a first edge to an upper edge of the rear wall and securedly attached at a second edge to an upper edge of the front wall with at least one (1) latch 20. The lid 12 when secured with the latches 20 effectively provides a seal to the environment from the interior 21. To affect this seal, a gasket may be used. More description of the basket 40 will be had below. Located superjacent to the heater element 25, and circumscribing an inner surface of the receptacle 11, is a shelf, configured to hold the basket 40.

Embedded or otherwise attached to the inner surface of the bottom wall of the receptacle 11 is a heating element 25. The heating element 25 is in electrical communication with a power supply via a power switch 13 and an adjustable thermostat 14. The power switch 13 provides selective power to the heating element 25 from a power source and the adjustable thermostat 14 provides a temperature regulating means. The power source can be an integral battery or a power cord. It is appreciated that any other means for regulating temperature, such as a rheostat, potentiometer, solid-state controller, can be used in place of the adjustable thermostat 14. A timer control circuit (not shown) is envisioned to be in electrical communication with the power switch 13, adjustable thermostat 14, and heating element 25. The timer control circuit can be pre-determined to enable a supply of power from the power source to the heating element 25 to affect a cleaning period. A first indicator light and a second indicator light 16 are also provided and in electrical communication with the power switch 13. The first indicator light 15 can preferably indicate that the appliance 10 is working (e.g., the heating element 25 is energized, the power switch 14 is activated, the timer control circuit is in control, etc.) and can be a green LED or colored lens. The second indicator light 16 can preferably indicate that the appliance 10 is off (e.g., the heating element is de-energized, the power switch 13 is activated, the timer control circuit has lapsed, etc.) and can be a red LED or colored lens. Essentially, the first indicator light 15 indicates the appliance 10 is "working" or "cleaning" or "on" and the second indicator light 16 indicates the appliance 10 is "done" or "contents are clean" or "off". It is preferred that the power switch 13, adjustable thermostat 14, first indicator light 15, and second indicator light 16 are located on the same face of the receptacle 11, herein illustrated as the front wall.

Immediately adjacent to the heating element 25 is a pan 30 or other similar reservoir to hold water or a cleaning solution therein. In some other embodiments, the pan 30 is integral with the heating element 25. In other embodiments, the pan 30 is arranged in such a manner so as to allow the heating element 25 to be immersed therewithin or otherwise in direct contact with the contents held therewithin. It is a desired object of the invention to enable the heating element 25, once energized, to heat the water or cleaning solution to a pre-determined temperature, a selected temperature by way of the adjustable thermostat 14, and/or a pre-determined time via the timer control circuit. Such a temperature can mimic that of a dishwasher or could reach the boiling point of water or the cleaning solution to create steam. The pan 28 is connected a door 23 located on a side of the receptacle 11. In another embodiment, the door 23 is not attached to the pan 28. A fill line 31 is imprinted or otherwise located about a circumferential inner surface of with the pan 28 or the receptacle 11, to indicate a maximum amount of water or cleaning solution to be placed therein without incidental contact of the water or cleaning solution onto the straws 100.

Figure 3:
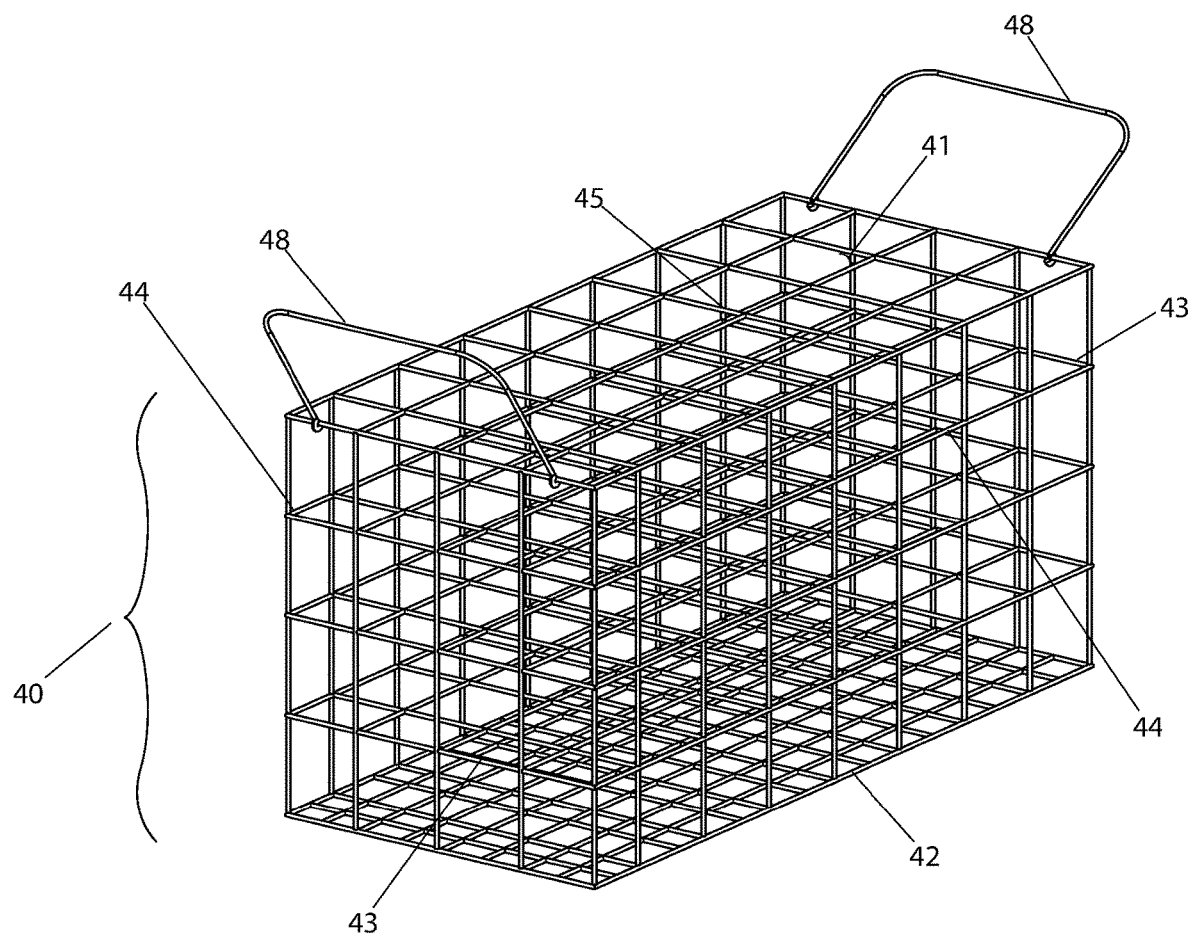
FIG. 3 is a perspective view of the basket 40, according to the preferred embodiment of the present invention; and, FIG. 4 is an electrical block diagram of the major components of the drinking straw sanitizing appliance drinking straw sanitizing appliance 10, according to the preferred embodiment of the present invention.

Regarding FIG. 3, the basket 40 is capable of being placed on and supported by the shelf. The basket 40 is preferably a metallic or plastic mesh shaped as a rectangular prism with a general shape of the receptacle 11 but having a height which enables the straws 100 to be held vertically therein without contacting the under surface of the lid 12. The basket 40 includes a basket top 41, a basket bottom 42, a pair of basket short sides 43, and a pair of basket long sides 44, to create a six-sided structure. The basket top 41 comprises a plurality of apertures 45 formed thereon. The apertures 45 may be arranged in any pattern, such as a matrix or random configuration. Each aperture 45 is sized to permit the passage of an individual straw 100 therethrough. Thus, the apertures 45 are sized and shaped to match the outer geometry and size of the straw 100. It is preferred that the apertures 45 provide minimal clearance for the straw 100 such that the straw 100 can remain as close as possible to a vertical upright orientation during the cleaning phase. The basket bottom 42 has a mesh or grid-like construction having apertures that do not permit the straws 100 from falling through and functions to effectively block the heating element 25 from physical contact with the contents in the basket 40, particularly the straws 100. It also functions to help maintain a vertical upright orientation for the straws 100 to maximize the sanitizing event. A pair of handles 48 are hingedly attached to the basket top 41.

The basket 40 preferably has an outer perimeter shape enabling it to fit within the space bounded by the internal surfaces of the side walls, rear wall, and front wall of the receptacle 11. The height of the lid 12 when in a closed position on the receptacle 11, is of a height to enable the uppermost ends of the contents (e.g., straws 100) to be fully within the interior 21 when standing in an upright position.

Referring now again to FIG. 1, some embodiments will have a vent 50 located on the lid 12, preferably in a central location. The vent 50 is preferably molded into or integral with the lid 12, such that there are no portions of the vent 50 that extend past the outer surfaces of the receptacle 11. In a preferred embodiment, the vent 50 includes a vent door 51 with a vent handle 52 that can open or close over the vent 50 when needed.

Figure 4:
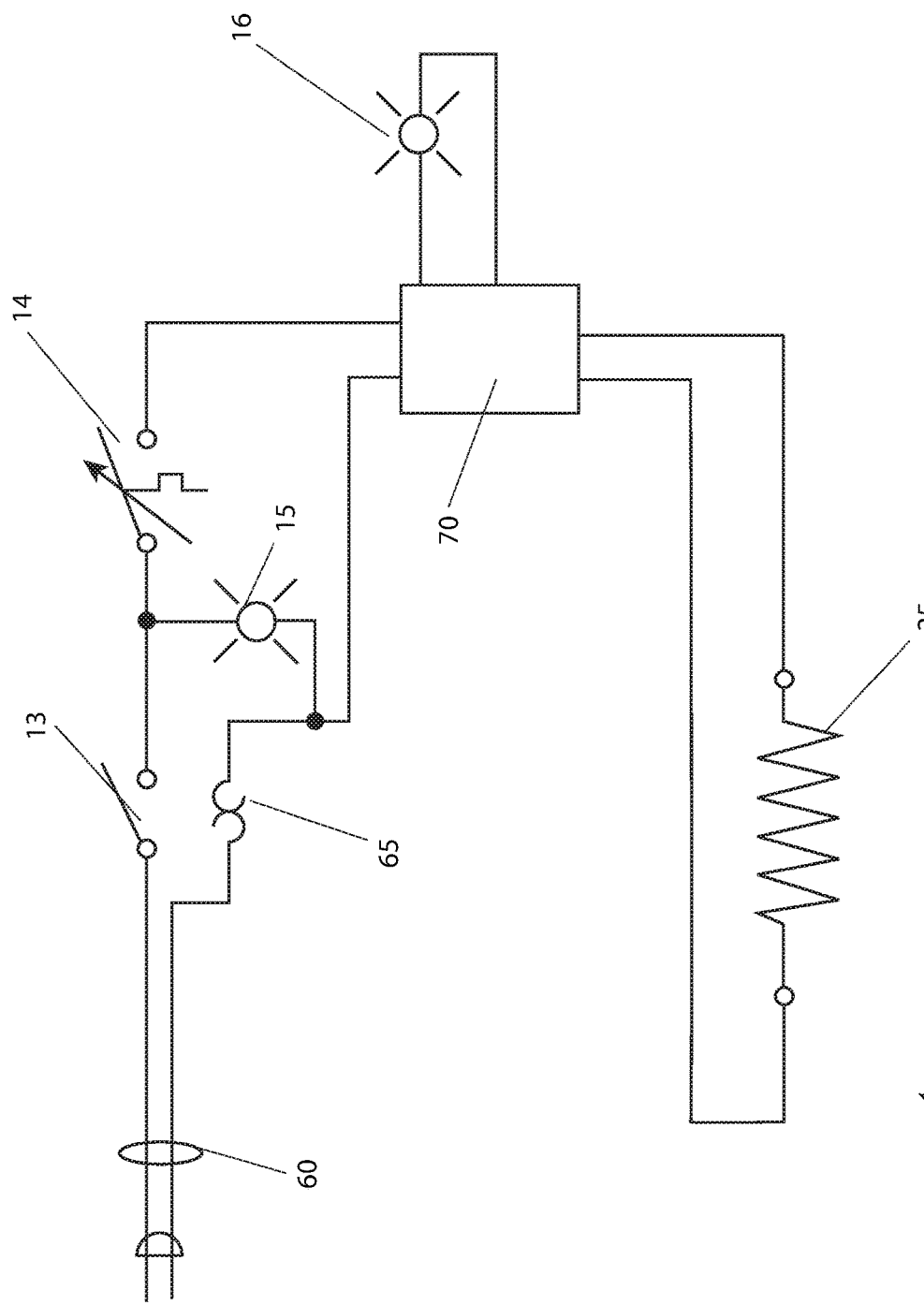

Referring to FIG. 4, an electrical block diagram of the major components of the drinking straw sanitizing appliance 10, according to the preferred embodiment of the present invention is shown. Power is derived from a power source 60, herein depicted as a power cord, but realizing that other sources of power such as a battery bank could be utilized with equal effectiveness. Said power is routed through the power switch 13 on the supply path and through a thermal overload protector 65 on the return leg. The controlled power then continues onto the adjustable thermostat 14, while a parallel path continues on to the first indicator light 15 to indicate power is applied to the drinking straw sanitizing appliance 10. Power is then sequentially routed to the timer control circuit 70 which directly controls the application of electrical power to the heating element 25. When the desired cleaning cycle is completed, as determined by the timer control circuit 70, the second indicator light 16 is then illuminated to notify the users that the straws 100 (as shown in FIG. 2) may be removed.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed:

1. A drinking straw sanitizing appliance, comprising:
   a receptacle having a heating element, the receptacle includes a bottom wall, a pair of side walls, a front wall, a rear wall, and an open top providing access to an interior of the receptacle thereof;
   a basket removably placed within the receptacle, the basket secures a plurality of drinking straws there within for cleaning, the basket includes a basket top, a basket bottom, a pair of basket short sides, and a pair of basket long sides, to create a six-sided structure;
   a lid hingedly attached at a first edge to an upper edge of the rear wall of the receptacle and securedly attached at a second edge to an upper edge of the front wall of the receptacle with at least one latch, the lid when secured with the at least one latch provides a seal to an environment from the interior of the receptacle, the lid also provides a covering for the interior of the receptacle;
   a vent having a vent door with a vent handle that opens or closes over the vent;
   a timer control circuit in electrical communication with a power switch, an adjustable thermostat, and the heating element;
   a first indicator light and a second indicator light provided in electrical communication with the power switch;
   a pan holding a quantity of water or cleaning solution therein adjacent to the heating element;
   a fill line imprinted about a circumferential inner surface of the pan to indicate a maximum amount of the quantity of water or cleaning solution placed therein without incidental contact of the quantity of water or cleaning solution onto the straws;
   wherein the heating element is located on a floor of the receptacle to heat the quantity of water or a cleaning solution in a steaming temperature or an elevated sanitizing temperature to render the drinking straws sanitary for reuse;
   wherein the heating element is in electrical communication with a power supply via the power switch and the adjustable thermostat; and
   wherein a shelf holds the basket that is located superjacent to the heating element and circumscribing an inner surface of the receptacle.

2. The drinking straw sanitizing appliance according to claim 1, wherein the receptacle is a rectangular prism.

3. The drinking straw sanitizing appliance according to claim 1, wherein the basket top includes a plurality of apertures formed thereon sized to permit passage of an individual straw therethrough.

4. The drinking straw sanitizing appliance according to claim 1, wherein the basket is made of a metallic mesh.

5. The drinking straw sanitizing appliance according to claim 1, wherein the basket is made of a plastic mesh.

6. The drinking straw sanitizing appliance according to claim 1, wherein the timer control circuit is pre-determined to enable a supply of power from a power source to the heating element to affect a cleaning period.

7. The drinking straw sanitizing appliance according to claim 1, wherein the first indicator light preferably indicates that the drinking straw sanitizing appliance is working.

8. The drinking straw sanitizing appliance according to claim 7, wherein the first indicator light is a green LED.

9. The drinking straw sanitizing appliance according to claim 1, wherein the second indicator light indicates that the drinking straw sanitizing appliance is off.

10. The drinking straw sanitizing appliance according to claim 9, wherein the second indicator light is a red LED.

11. The drinking straw sanitizing appliance according to claim 1, wherein the power switch, the adjustable thermostat, the first indicator light, and the second indicator light are located on the front wall of the receptacle.

12. The drinking straw sanitizing appliance according to claim 1, wherein the heating element is embedded to the floor of the receptacle.

13. The drinking straw sanitizing appliance according to claim 1, wherein the heating element is attached to the floor of the receptacle.

14. The drinking straw sanitizing appliance according to claim 1, wherein the power switch provides selective power to the heating element from the power supply.

15. The drinking straw sanitizing appliance according to claim 1, wherein the power source is an integral battery.

16. The drinking straw sanitizing appliance according to claim 1, wherein the power source is configured to engage in electrical communication with an electrical outlet.

17. The drinking straw sanitizing appliance according to claim 1, wherein the basket bottom has a mesh or a grid-like construction having a plurality of apertures that do not permit the straws from falling through and functions to effectively block the heating element from physical contact with the straws in the basket and maintains a vertical upright orientation for the straws to maximize a sanitizing event.

* * * * *